(12) United States Patent
Kwok et al.

(10) Patent No.: US 8,879,060 B2
(45) Date of Patent: Nov. 4, 2014

(54) RAMAN SIGNAL DETECTION AND ANALYSING SYSTEM AND A METHOD THEREOF

(71) Applicant: Hong Kong Applied Science and Technology Research Institute Co. Ltd., New Territories (HK)

(72) Inventors: Ka Cheung Kwok, New Territories (HK); Lut Hey Chu, New Territories (HK); Chun Zhang, New Territories (HK); Lap Wai Lydia Leung, New Territories (HK)

(73) Assignee: Hong Kong Applied Science and Technology Research Institute Company Limited, Shatin (HK)

( * ) Notice: Subject to any disclaimer, the term of this patent is extended or adjusted under 35 U.S.C. 154(b) by 65 days.

(21) Appl. No.: 13/854,975

(22) Filed: Apr. 2, 2013

(65) Prior Publication Data

US 2014/0293279 A1 Oct. 2, 2014

(51) Int. Cl.
*G01J 3/44* (2006.01)
*G01N 21/65* (2006.01)

(52) U.S. Cl.
CPC ..................... *G01N 21/65* (2013.01)
USPC ....................................................... 356/301

(58) Field of Classification Search
CPC ................ G01N 21/65; G01N 21/658; G01N 2021/656; G01J 3/44; G01J 3/02
USPC ........................................................ 356/301
See application file for complete search history.

(56) References Cited

U.S. PATENT DOCUMENTS

| | | | |
|---|---|---|---|
| 3,963,351 A | 6/1976 | Chance et al. | |
| 5,351,117 A * | 9/1994 | Stewart et al. | .................. 356/30 |
| 5,754,289 A | 5/1998 | Dou et al. | |
| 5,995,858 A | 11/1999 | Kinast | |
| 7,423,749 B2 | 9/2008 | Hagler | |
| 7,777,878 B2 | 8/2010 | Liphardt | |
| 2007/0049809 A1 | 3/2007 | Bechtel et al. | |
| 2007/0060806 A1 | 3/2007 | Hunter et al. | |
| 2009/0316137 A1 | 12/2009 | Shioi | |
| 2011/0128538 A1 * | 6/2011 | Cerullo et al. | ................ 356/301 |
| 2012/0035442 A1 | 2/2012 | Barman et al. | |
| 2012/0203114 A1 * | 8/2012 | Bechtel et al. | ................ 600/476 |

* cited by examiner

*Primary Examiner* — Tarifur Chowdhury
*Assistant Examiner* — MD Rahman
(74) *Attorney, Agent, or Firm* — Eagle IP Limited; Jacqueline C. Lui (57) ABSTRACT

A Raman signal detection and analyzing system and a method thereof are disclosed. The Raman signal is generated by emitting an excitation light to a sample. The Raman signal is then modulated by passing through a plurality of optical filter and modulator. The resulting modulated Raman signal comprises two orthogonal components, which intensities are to be computed based on the first harmonic of said modulated Raman signal. The content of a specific analyte within the sample can then be determined based on the ratio of the intensities of the two components.

18 Claims, 10 Drawing Sheets

RAMAN SIGNAL DETECTION AND ANALYSING SYSTEM AND A METHOD THEREOF

FIELD OF INVENTION

This invention relates to a measuring instrument and in particular a measuring instrument for detecting a content of an analyte in a sample by analyzing Raman signal with internal standard method.

BACKGROUND OF INVENTION

Raman spectroscopy is a powerful tool for quantitative analysis of the composition and concentration of a certain analyte within a sample. In the application of physiological detection, such an optical measurement is usually carried out in the near-infrared region. The Raman signal is often small, for instance the ratio of Raman signal strength to excitation signal strength is less than $10^{-10}$. Moreover the Raman signal is ultra-sensitive to the measurement conditions, such as laser fluctuation, optical bleaching, temperature variation, the changes in sample size and sample shape and optical alignment. Therefore internal standard method is usually applied during the analysis of the Raman signal. The basic principle of internal standard method is to measure a sample signal and a standard signal simultaneously (or nearly simultaneously) and their ratio, which is invariant from the measurement conditions, is used in the quantitation. Conventionally, a Grating-CCD (or Grating-photodiode-array) spectrometer is used as the detector in these systems. However, these systems are expensive and throughput is limited by the grating at required spectral resolution.

Recent developments in Microelectromechanical systems (MEMS)-based spectrometer made it possible to use single detector to replace the CCD system in Raman signal detection system which significantly reduces the system cost. However, the throughput of such single-detector system is still limited by the use of grating. In order to achieve high throughput system, different designs have been disclosed. One of such design uses a sweeping light source, for instance a tunable laser, to obtain the Raman spectrum. Another approach uses a tunable filter, for instance an acousto-optical tunable filter, to obtain the Raman spectrum. Nonetheless, the costs of these new designs are not acceptable in constructing a home-used device for monitoring physiological parameters.

SUMMARY OF INVENTION

In the light of the foregoing background, it is an object of the present invention to provide an alternative design of low-cost, high-throughput Raman signal detection and analyzing system.

Accordingly, the present invention, in one aspect, provides a method of determining the content of an analyte in a sample based on Raman signal. The Raman signal is first generated by emitting an excitation light to the sample. The Raman signal is then modulated by passing the Raman signal through a plurality of optical filters and modulators. The modulated Raman signal comprises a first component and a second component, wherein the two components are orthogonal to each other. The intensities of the two components are then computed based on the first harmonic of the modulated Raman signal. Finally, the content of said analyte is determined based on the ratio of the intensities of the two components.

In an exemplary embodiment of the present invention, the first component and second component are in the first quadrant and second quadrant of the modulated Raman signal respectively.

In another aspect of the present invention, another method of determining the content of an analyte in a sample based on Raman signal is provided. An excitation light comprising a first and second wavelength is first generated. The excitation light is then modulated by passing the excitation light through a plurality of optical filters and modulators. A Raman signal is generated afterwards by directing the modulated light to the sample. The Raman signal generated comprises a first component and a second component, wherein the two components are orthogonal to each other. The intensities of the two components are then computed based on the first harmonic of the modulate Raman signal. Finally, the content of said analyte is determined based on the ratio of the intensities of the two components.

A measuring instrument for detecting a content of an analyte in a sample based on Raman signal is also provided in another aspect of the present invention. The system comprises of an excitation light source for irradiating said sample and generating an optical signal; an optical module configured to generate a modulated Raman signal from the optical signal; a detector configured to receive the modulated Raman signal; a microprocessor coupled to the detector; and a computer-readable storage medium coupled to the microprocessor.

In a specific embodiment of the prevent invention, the computer-readable storage medium encoded with computer-readable instructions for causing said microprocessor to execute the following steps: (i) demodulating the modulated Raman signal in order to determine the intensities of the first component and said second component based on the first harmonic of the modulated Raman Signal; and (ii) computing said content of said analyte based on said intensities of said first component and said second component.

With such an operation in modulation and demodulation of the two signals, the Raman detection with internal standard method can be implemented with weak signals. Another advantage of the present invention is that it only contains a single detector which significantly cut down the cost of the Raman detection system. Furthermore, the throughput of the present invention is higher and the measured target/standard ratio is more stable comparing with those in the conventional setup as there is no dispersive component, such as a grating. Last but not least, the simple signal decomposition algorithm enable the cost of the overall system to be further reduced.

BRIEF DESCRIPTION OF FIGURES

FIG. 1 show schematic diagrams of the measuring instrument according to one embodiment of the present invention in (a) transmission mode and (b) reflectance mode.

FIG. 3 show schematic diagrams of the optical module of the present invention with (a) flipping mirror, (b) chopping wheel and (c) liquid crystal shutters.

DETAILED DESCRIPTION OF THE PREFERRED EMBODIMENTS

As used herein and in the claims, "comprising" means including the following elements but not excluding others.

Figure 1A:
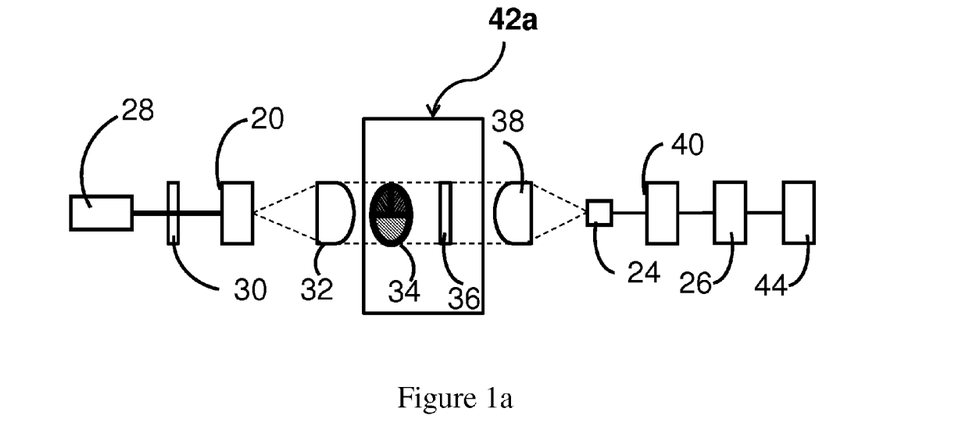

Referring now to FIG. 1a, an apparatus according to the present invention in post-filtering transmission mode is illustrated.

The system in transmission mode broadly includes an excitation light source 28, a laser line filter 30, a collimating lens 32, an optical module 42, a detector 24, a signal processing unit 40, a microprocessor 26 and a computer readable storage medium 44. The detector 24 is coupled to the signal processing unit 40, which is further coupled to the microprocessor 26. The computer readable storage medium 44 is coupled to the microprocessor 26.

The excitation light source 28 are configured to emit at least one excitation light at the excitation wavelength $\lambda_E$ to a sample 20 to be measured after passing through one or two laser line filters 30. An optical signal, particularly, a Raman signal will be emitted from the sample 20 as a result of the excitation light. In one embodiment, the optical module 42a further includes a filter wheel 34 and one or two notch filters 36. The Raman signal emitted then reaches the filter wheel 34 through the collimating lens 32, which is used to collimate the Raman signal generated from the sample. The filter wheel 34 is connected to a motor (not shown) configured to rotate the filter wheel 34 at a predetermined period or frequency. The Raman signal is filtered at two predetermined spectral regions by two optical filters and periodically passes through the filter wheel 34 for n periods during a circle of the wheel rotation (wherein n>=1). The filter wheel 34 is rotated such that it allows the Raman signal passing through a first optical filter 48a at spectral range of the sample signal $\lambda_{S1}$ at a first quadrant to obtain a first component (i.e. sample signal). The filter wheel 34 further allows the Raman signal passing through a second optical filter 50a at spectral range of standard signal $\lambda_{S2}$ at a second quadrant to obtain a second component (i.e. standard signal). In addition, the filter wheel 34 does not allow the Raman signal from reaching the detector 24 for the remaining period of time. As a result, the sample Raman signal and the standard Raman signal are given by Raman Shift (sample)

$$= \frac{1}{\lambda_E} - \frac{1}{\lambda_{S1}},$$

and

Raman shift (standard)

$$= \frac{1}{\lambda_E} - \frac{1}{\lambda_{S2}},$$

respectively

While the filter wheel 34 rotates at a period T, the sample signal and the standard signal are modulated at the same period T yet with a phase difference of $\lambda/2$. The filter wheel 34 thereby modulates the Raman signal by a first periodic function to obtain the first component and modulated the Raman signal by a second periodic function to obtain the second component. The first periodic function and the second periodic function have the same period and are orthogonal to each other. The modulated Raman signal then passes through the one or two notch filters 36 and the converging lens 38 to reach at the detector 24. The converging lens 38 focuses the modulated Raman signal into the detector 24. The modulated Raman signal is then converted to electric signal at the detector 24. The electric signal is then transferred to the signal processing unit 40. The signal processing unit 40 filters and amplifies this analog electric signal and converts it into digital signal. The digital signal is then demodulated at the microprocessor 26 by computing the intensities of the first component and the second component based on the first harmonic of said modulated Raman Signal. Finally the content of the analyst within the sample can be calculated by computing the ratio between the intensity of the first component and the second component. A computer-readable storage medium 44 is coupled to the microprocessor 26. The computer-readable storage medium 44 is encoded with computer-readable instructions for causing the microprocessor 26 to execute the aforesaid demodulation and ratio calculation.

In one specific embodiment, a focusing lens can be inserted between the laser line filter 30 and the sample 20 if the excitation light beam spot is not sufficiently small. In another specific embodiment, the one or two laser line filters 30 can be replaced with one or two short-pass edge filters in order to lower the cost. In yet another specific embodiment, the one or two notch filters 36 can be replaced with one or two long-pass edge filters in order to lower the cost. In further another specific embodiment, the collimating lens 32 and the converging lens 38 can be replaced with reflective optical components, for example, concave mirrors, in order to improve the light collection efficiency and reduce the unwanted Raman or fluorescence light generated from the lenses. In yet another specific embodiment, the motor is a stepping motor. In yet another specific embodiment, the signal processing unit 40 is integrated with the microprocessor 26.

Figure 1B:
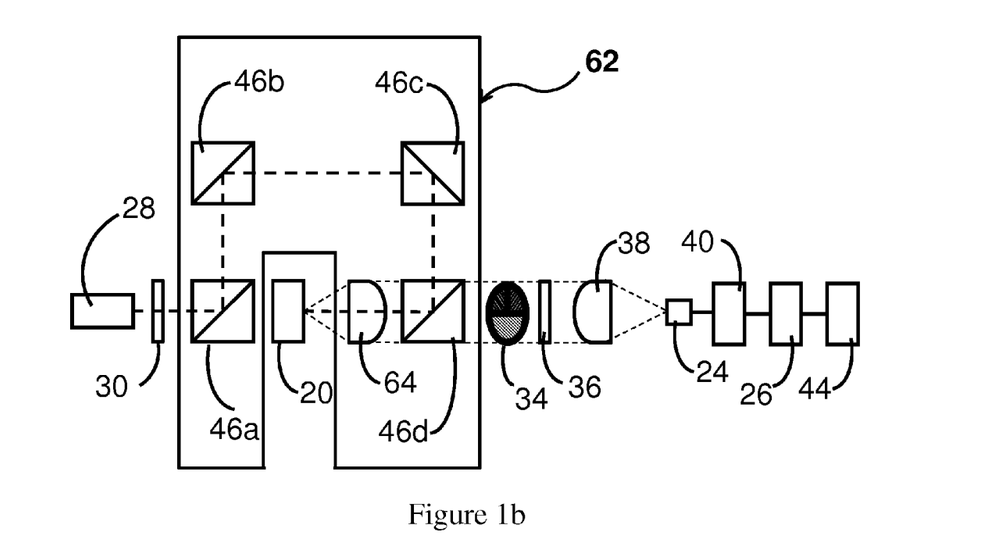

Referring now to FIG. 1b, an apparatus according to the present invention in post-filtering reflectance mode is illustrated.

The system in reflectance mode broadly includes all the elements as described in the transmission mode except replacing the collimating lens 32 by a reflectance module 62. A plurality of dichroic mirrors 46 and a converging lens 64 are included in the reflectance module 62.

The at least one excitation light emitted from the excitation light source 28 at the excitation wavelength $\lambda_E$ is guided to excite a predetermined surface of the sample by the reflectance module 62 after passing through the laser line filter 30. An optical signal, particularly, a Raman signal will be emitted from the excited surface of the sample 20 as a result of the excitation light. The Raman signal emitted then reaches the filter wheel 34 through the converging lens 64 and the dichroic mirror 46d of the reflectance module 62. The filter wheel 34 and all elements in the system in reflectance mode operate the same way as described in the system in transmission mode above.

In another specific embodiment, the one or two laser line filters 30 can be replaced with one or two short-pass edge filters in order to lower the cost. In yet another specific embodiment, the one or two notch filters 36 can be replaced with one or two long-pass edge filters in order to lower the cost. In further another specific embodiment, the converging lens 64 and the converging lens 38 can be replaced with reflective optical components, for example, concave mirrors, in order to improve the light collection efficiency and reduce the unwanted Raman or fluorescence light generated from the lenses. In further another specific embodiment, the three dichroic mirrors 46*a-c* can be replaced with three mirrors that direct the laser beam.

FIGS. 2*a-f* illustrate different embodiments of the filter wheel 34 used in the present invention. The filter wheels 34 illustrated have at least one compartment 66. A compartment 66 includes four contiguous parts. A first optical filter 48 and a second optical filter 50 are mounted on the first two adjacent contiguous parts of the compartment 66.

Figures 2A, 2D:
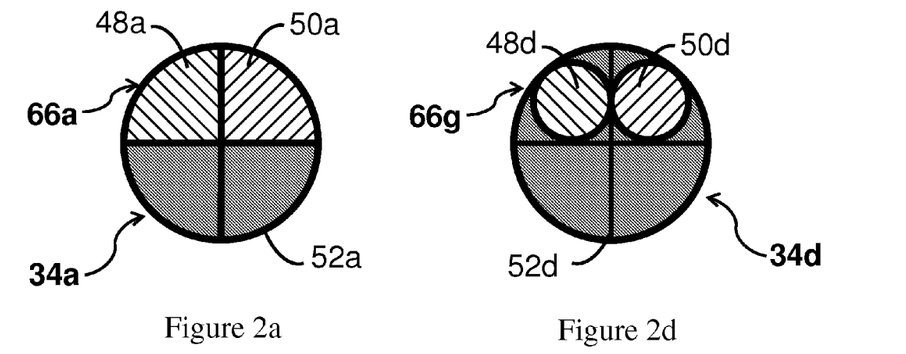
FIGS. 2a-2f show the filter wheels according to different embodiments of the present invention.
Figure 2B:
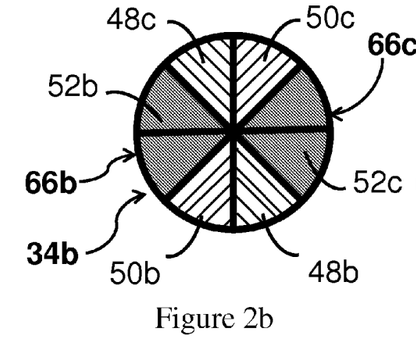
Figure 2C:
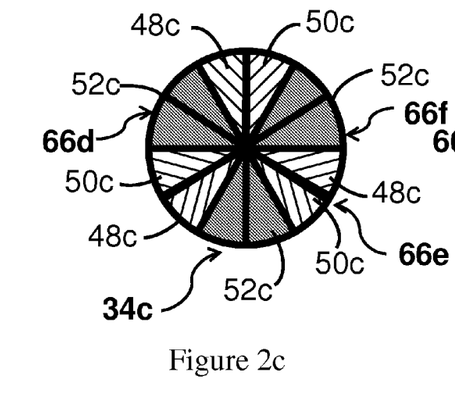
Figure 2E:
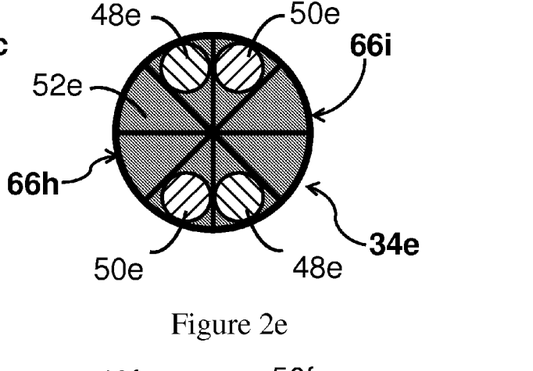
Figure 2F:
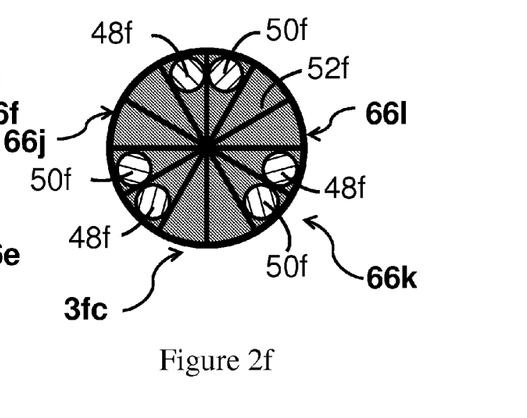

FIG. 2*a* shows a filter wheel 34*a* having one compartment 66*a*. A first optical filter 48*a* and a second optical filter 50*a* are mounted to the first and second part, which is adjacent to the first part of the compartment 66*a*. The remaining parts are filled with material 52*a* that disable the Raman signal to pass through the filter wheel 34*a*. The material 52*a* used for disabling the Raman signal to pass through can be, but not limited to, non-transparent plastic or paper. One skilled in the art would understand that any other material can be used as long as it can disable the Raman signal to pass through. FIG. 2*b* shows a filter wheel 34*b* having two compartments 66*b* and 66*c*. A first optical filter 48*b* and second optical filter 50*b* are mounted to the first and second part of the compartment 66*b*. A third optical filter 48*c* and forth optical filter 50*c* are mounted to the first and second part of the compartment 66*c*. In FIG. 2*c*, three compartments 66*d*, 66*e* and 66*f* are formed in a filter wheel 34*c*. A first and second optical filter 48*d*, 50*d*; a third and fourth optical filter 48*e*, 50*e*; and a fifth and sixth optical filter 48*f*, 50*f* are mounted to the first and second part of the compartments 66*d*, 66*e* and 66*f* respectively. The optical filters 48 and 50 in the filter wheels 34*a-c* substantially fully cover the whole first and second parts of the compartments. In alternative embodiment, the filter wheels 34*d*, 34*e* and 34*f* shown in FIGS. 2*d-2f* are constructed the same way as the filter wheels 34*a*, 34*b* and 34*c* as illustrated in FIGS. 2*a-2d* except that the optical filters in filter wheels 34*d*-34*e* only partially cover the first and second parts of the compartments. The optical filters can be in any shape. In one embodiment, the optical filters are in circular shape. In another embodiment, the optical filters are in arc-shape. In one specific embodiment, the filter wheel 34 can be in other shape.

Figure 3A:
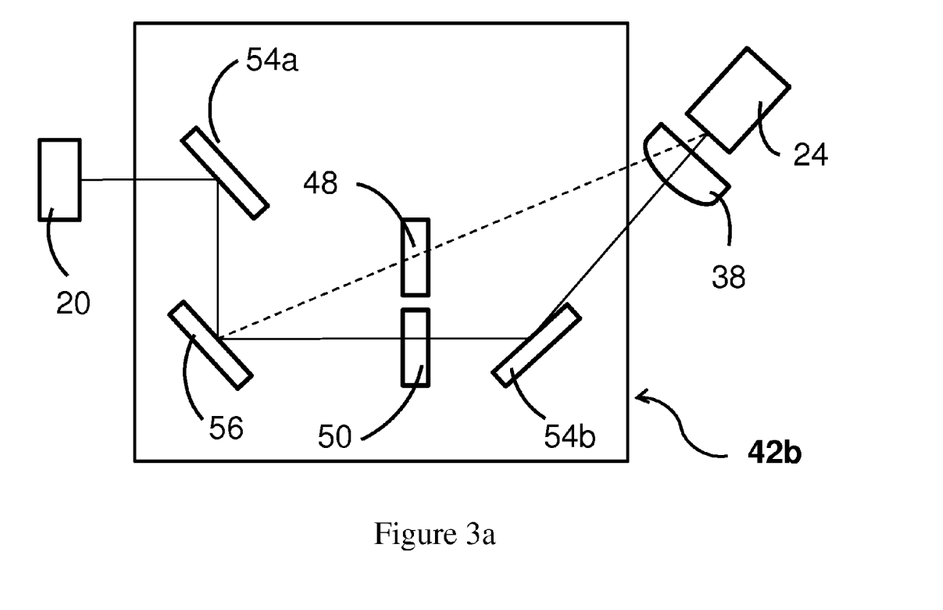
Figure 3B:
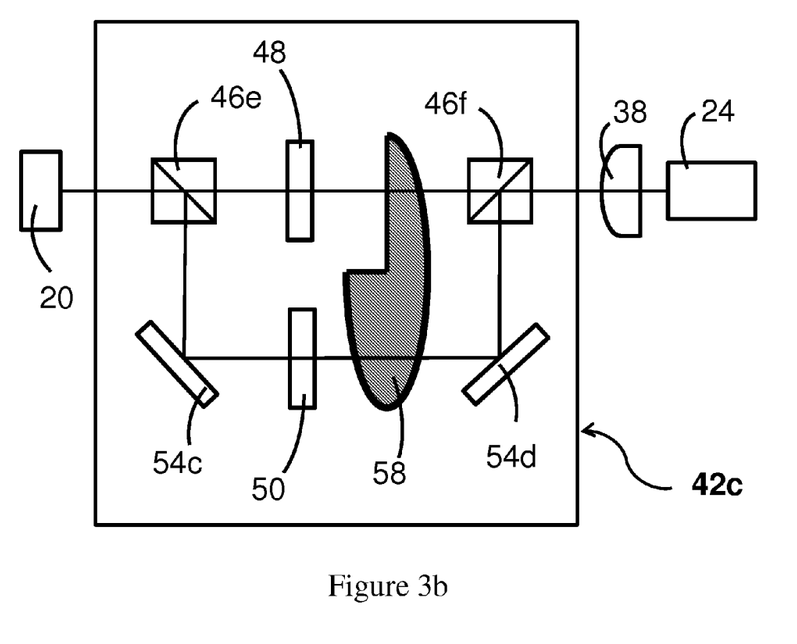
Figure 3C:
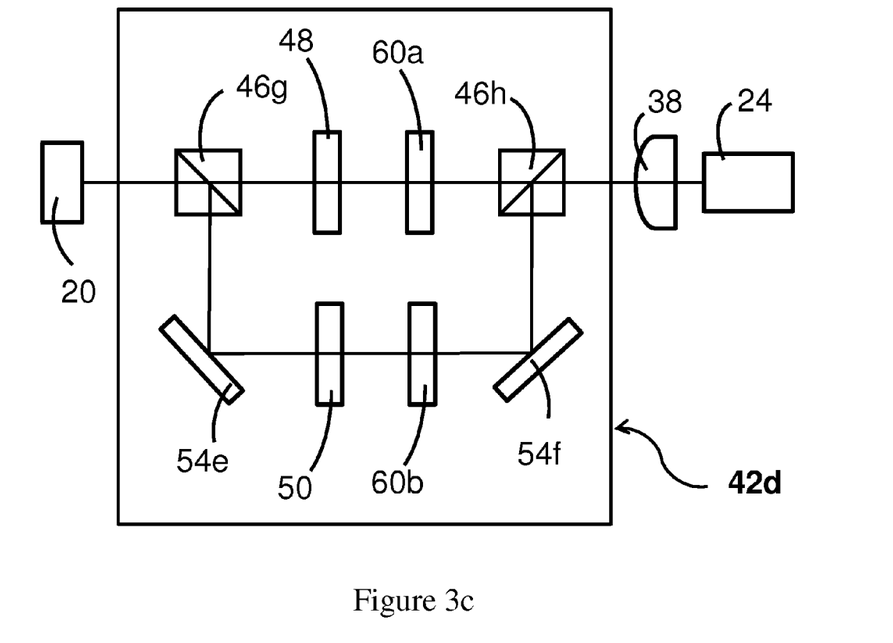

FIGS. 3*a*-3*c* illustrate different embodiments of the optical module 42 of the present invention.

FIG. 3*a* shows another embodiment of an optical module 42*b* comprises a first mirrors 54*a*, a second mirror 54*b*, a first optical filter 48, a second optical filter 50 and a flipping mirror 56. The first mirror 54*a* is configured to reflect the Raman signal emitted from the sample to the flipping mirror 56. The Raman signal is then directed to either the first optical filter 48 at spectral range of the sample signal $\lambda_{S1}$, the second optical filter 50 at spectral range of the standard signal $\lambda_{S2}$ or an empty space by the flipping mirror 56 in predetermined timeslots. The flipping mirror 56 is coupled to a motor (not shown), which flips the flipping mirror 56 at different position at different timeslot to achieve the above mentioned purposes. In one specific embodiment, the flipping mirror 56 flips at a predetermined period. The motor first flips the flipping mirror 56 at first position for a first quadrant such that the Raman signal is directed to pass through the first optical filter 48 to obtain a first component. The first component is then directed to the detector 24 through a diverging lens 38. After that the motor flips the flipping mirror 56 at a second position for a second quadrant such that the Raman signal is directed to pass through the second optical filter 50 to obtain a second component. The second component is then guided to the detector 24 through the second mirror 54*b* and the converging lens 38. Finally, the motor flips the flipping mirror 56 at a third position for the remaining amount of time of the period so that no component is able to reach the detector 24. In summary, the flipping mirror 56 is flipped such that it allows the Raman signal passing through the first optical filter 48 at spectral range of the sample signal $\lambda_{S1}$ at first quadrant to obtain the first component (i.e. sample signal). The flipping mirror 56 further allows the Raman signal passing through the second optical filter 50 at spectral range of standard signal $\lambda_{S2}$ at the second quadrant to obtain the second component (i.e. standard signal). In addition, the flipping mirror 56 does not allow the Raman signal from reaching the detector 24 for the remaining period of time. As a result, the sample Raman signal and the standard Raman signal are given by Raman Shift (sample)

$$= \frac{1}{\lambda_E} - \frac{1}{\lambda_{S1}},$$

and
Raman shift (standard)

$$\text{Raman shift (standard)} = \frac{1}{\lambda_E} - \frac{1}{\lambda_{S2}}$$

respectively

While the flipping mirror 56 is flipped at a period T, the sample signal and the standard signal are modulated at the same period T yet with a phase difference of $\pi/2$. The flipping mirror 56, the first optical filter 48 and the second optical filter 50 thereby cooperate to modulate the Raman signal by a first periodic function to obtain the first component and modulate the Raman signal by a second periodic function to obtain the second component. The first periodic function and the second periodic function have the same period T and are orthogonal to each other.

FIG. 3*b* shows yet another embodiment of an optical module 42*c* including a first dichroic mirror 46*e*, a second dichroic mirror 46*f*, a first mirror 54*c*, a second mirror 54*d*, the first optical filter 48 at spectral range of the sample signal $\lambda_{S1}$, the second optical filter 50 at spectral range of standard signal $\lambda_{S2}$ and a chopping wheel 58. The Raman signal emitted from the sample is firstly split into two beams of the Raman signal by the dichroic mirror 46*e*. The first beam of the Raman signal then passes through the first optical filter 48 to obtain a first component (i.e. sample signal) and the second beam of the Raman signal is then guided to pass through the second optical filter 50 by the first mirror 54*c* to obtain a second component (i.e. standard signal). The chopping wheel 58 is coupled to a motor (not shown) and is rotated at a predetermined period and is configured to block the first and second components from reaching the detector 24 for a predetermined period of time. The chopping wheel 58 has an opening section which allows the first component to pass through at a first predetermined period of time and allows the second component to pass though at a second predetermined period of time. In one specific embodiment, the chopping wheel 58 is rotated at a predetermined period. The opening section occupies a portion of the chopping wheel 58 such that: at the first quadrant, the opening section allows the first component to pass through so that the first component reaches the detector 24 through the second dichroic mirror 46*f* and the converging lens 38; at the second quadrant, the opening section allows the second component to pass through so that the second component reaches the detector 24 through the second dichroic mirror 46*f* and the converging lens 38. The mirror 54*d* is used to guide the second component to the second dichroic mirror 46f after passing through the opening section of the chopping wheel 58; and for the remaining of the period, no component is able to reach the detector 24. As a result, the sample Raman signal and the standard Raman signal are given by Raman Shift (sample)

$$\text{Raman Shift (sample)} = \frac{1}{\lambda_E} - \frac{1}{\lambda_{S1}},$$

and
Raman shift (standard)

$$\text{Raman shift (standard)} = \frac{1}{\lambda_E} - \frac{1}{\lambda_{S2}}$$

respectively

While the chopping wheel 58 is rotated at a period T, the sample signal and the standard signal are modulated at the same period T yet with a phase difference of π/2. The chopping wheel 58, the first optical filter 48 and the second optical filter 50 thereby modulated the Raman signal by a first periodic function to obtain the first component and modulated the Raman signal by a second periodic function to obtain the second component. The first periodic function and the second periodic function have the same period and are orthogonal to each other. In another specific embodiment, the chopping wheel 58 is placed ahead of the first optical filter 48 and the second optical filter 50 thereby modulating the Raman signal by a first and second periodic function before passing through the first optical filter 48 and the second optical filter 50.

FIG. 3c shows yet another embodiment of an optical module 42d. The optical module 42d includes a first dichroic mirror 46g, a second dichroic mirror 46h, a first mirror 54e, a second mirror 54f, a first optical filter 48 at spectral range of the sample signal $\lambda_{S1}$, a second optical filter 50 at spectral range of standard signal $\lambda_{S2}$ and a pair of electronic optical shutters 60a and 60b. The Raman signal emitted from the sample is firstly split into two beams of Raman signal by the dichroic mirror 46g. The first beam of Raman signal then passes through a first optical filter 48 to obtain a first component (i.e. sample signal) and the second beam of Raman signal is then guided to pass through second optical filter 50 by the first mirror 54e to obtain a second component (i.e. standard signal). The electronic optical shutters 60a and 60b are controlled by an electronic controller (not shown) to selectively switching the optical shutters 60a and 60b to block the first component and second component from reaching the detector 24 separately. In one specific embodiment, the electronic optical shutters 60a and 60b are liquid crystal optical shutters 60a and 60b. The liquid crystal optical shutters 60a and 60b are opened and closed at a predetermined period of time independently. At the first quadrant, the first liquid crystal optical shutter 60a is opened while the second liquid crystal optical shutter 60b is closed such that only the first component is allowed to pass through so that the first component reaches the detector 24 through the dichroic mirror 46h and the converging lens 38. At the second quadrant, the first liquid crystal optical shutter 60a is closed while the second liquid crystal optical shutter 60b is opened such that only the second component is allowed to pass through so that the second component reaches the detector 24 through the dichroic mirror 46h and the converging lens 38. The mirror 54f is used to guide the second component to the dichroic mirror after passing through the second liquid crystal optical shutter 60b. For the remaining of period of time, both shutters 60a and 60b are closed so that no component is able to reach the detector at the remaining period of time. As a result, the sample Raman signal and the standard Raman signal are given by Raman Shift (sample)

$$\text{Raman Shift (sample)} = \frac{1}{\lambda_E} - \frac{1}{\lambda_{S1}},$$

and
Raman shift (standard)

$$\text{Raman shift (standard)} = \frac{1}{\lambda_E} - \frac{1}{\lambda_{S2}}$$

respectively

While the first and second electronic shutters 60 are opened/closed independently or dependently at a period T, the sample signal and the standard signal are modulated at the same period T yet with a phase difference of π/2. The electronic shutters 60a and 60b, the first optical filter 48 and the second optical filter 50 thereby modulated the Raman signal by a first periodic function to obtain the first component and modulated the Raman signal by a second periodic function to obtain the second component. The first periodic function and the second periodic function have the same period and are orthogonal to each other. In another specific embodiment, the first and second electronic shutters 60 are placed ahead of the first optical filter 48 and the second optical filter 50 thereby modulating the Raman signal by a first and second periodic function before passing through the first optical filter 48 and the second optical filter 50.

In one specific embodiment for the embodiments of the optical modules 42 (i.e. the optical modules of flipping mirror 56, the chopping wheel 58, or electronic shutters 60), microprocessor 26 is coupled to the optical module 42. The microprocessor 26 operates the optical module 42 to generate the modulated Raman signal, wherein the modulated Raman signal comprises the first component and the second component, and the first component and the second component are orthogonal to each other. In specific, the microprocessor 26 is coupled to the motor (not shown) for the flipping mirror 56 or the chopping wheel 58 to operate the flipping mirror 56 or the chopping wheel 58. In case of the electronic shutters 60, the microprocessor 26 is coupled to the controller (not shown) to operate the electronic shutters 60 (e.g. liquid crystal). In yet another specific embodiment, the motor used in the optical modules 42 of flipping mirror 56 or the chopping wheel 58, is a stepping motor.

Figure 4:
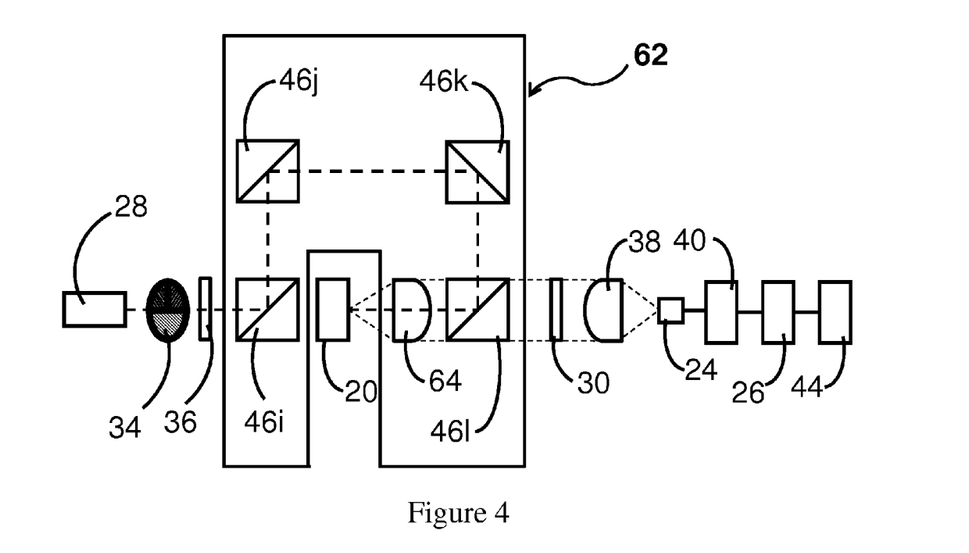
FIG. 4 shows a schematic diagram of the measuring instrument according to another embodiment of the present invention in reflectance mode.

FIG. 4 illustrates an apparatus according to the present invention in pre-filtering mode.

The system in pre-filtering mode broadly includes an excitation light source 28, one or two laser line filters 30, a converging lens 38, a filter wheel 34, one or two notch filters 36, a reflectance module 62, a detector 24, a signal processing unit 40, a microprocessor 26 and a computer readable storage medium 44. The detector is coupled to the signal processing unit 40, which is further coupled to the microprocessor 26. The computer readable storage medium 44 is coupled to the microprocessor 26.

The excitation light source 28 is configured to emit an excitation light with at least two wavelengths to a sample through the one or two notch filters 36 and the reflectance module 62. The filter wheel 34 is connected to a motor (not shown) configured to rotate the filter wheel 34 at a predetermined period. The filter wheel 34 is rotated such that it allows the excitation light through a first optical filter 48a at first quadrant to obtain a first sub-excitation light with a first wavelength. The filter wheel 34 further allows the excitation light though a second optical filter 50a at the second quadrant to obtain a second sub-excitation light with a second wavelength. Thereby a modulated excitation light is generated by the filter wheel 34. In other words, the filter wheel 34 modulates the excitation light by a first periodic function to obtain the first sub-excitation light and modulates the excitation light by a second periodic function to obtain the second sub-excitation light. The first periodic function and the second periodic function have the same period and are orthogonal to each other. The operation of the reflectance module 62 has been described above in the system in reflectance mode and thus not being repeated here. A modulated Raman signal is generated once the modulated excitation light reaches the sample. A first component (i.e. sample signal) of a modulated Raman signal is generated when the first sub-excitation light interacts with the sample and a second component (i.e. standard signal) of a modulated Raman signal is generated when the second sub-excitation light interacts with the sample.

While the filter wheel 34 rotates at a period T, the sample signal and the standard signal are generated at the same period T yet with a phase difference of $\pi/2$. The modulated Raman signal emitted will then reaches the detector 24 through the converging lens 64 and the dichroic mirror 46l of the reflectance module 62, one or two laser line filters 30 and a converging lens 38. The modulated Raman signal is then converted to electric signal at the detector 24. The electric signal is then transferred to the signal processing unit 40. The signal processing unit 40 filters and amplifies this analog electric signal and converts it into digital signal. The digital signal is then demodulated at the microprocessor 26 by computing the intensities of the first component and the second component based on the first harmonic of said modulated Raman Signal. Finally the content of the analyst within the sample can be calculated by computing the ratio between the intensity of the first component and the second component. A computer-readable storage medium 44 is coupled to the microprocessor 26. The computer-readable storage medium 44 is encoded with computer-readable instructions for causing the microprocessor 26 to execute the aforesaid demodulation and ratio calculation. In yet another specific embodiment, the signal processing unit 40 is integrated with the microprocessor 26.

In one specific embodiment, instead of a fixed wavelength laser, a light source containing at least two predetermined wavelengths, e.g., a tungsten lamp or a broadband LED lamp or a two-color LED lamp, is used as the excitation light source. Then the excitation light passes through the rotating filter wheel 34 containing one bandpass filter in the spectral wavelength for generating sample signal $\lambda_{E1}$ (e.g., 1064±5 nm optical filter), and the other bandpass filter in the spectral wavelength for generating standard signal $\lambda_{E2}$ (e.g. 1010±5 nm optical filter). Then the modulated dual-wavelength excitation light passes through one or two notch filters 36 that reject the impurity lights that overlap with spectral wavelength of the Raman signal $\lambda_S$ (e.g., rejecting 1210±10 nm optical notch filter). The Raman signal generated from the sample is filtered through one or two laser line filters 30 (e.g. 1210±5 nm optical filter) before reaching to the detector 24. As a result, the sample Raman signal and the standard Raman signal are given by Raman Shift (sample)

$$\text{Raman Shift (sample)} = \frac{1}{\lambda_{E1}} - \frac{1}{\lambda_S},$$

and
Raman Shift (standard)

$$\text{Raman Shift (standard)} = \frac{1}{\lambda_{E2}} - \frac{1}{\lambda_S}$$

respectively.

The three dichroic mirrors 46i-k can be replaced with three mirrors that direct the laser beam. The excitation light can be modulated by, but not limited to, using the optical modules 42 as described above. The notch filters 36 can be substituted with two short-pass filters (e.g., <1100 nm optical filter). In addition, the reflectance module 62 in the pre-filtering mode system can be replaced by a collimating lens 32 in making a pre-filtering transmission mode system (not shown in the figures).

Figure 5A:
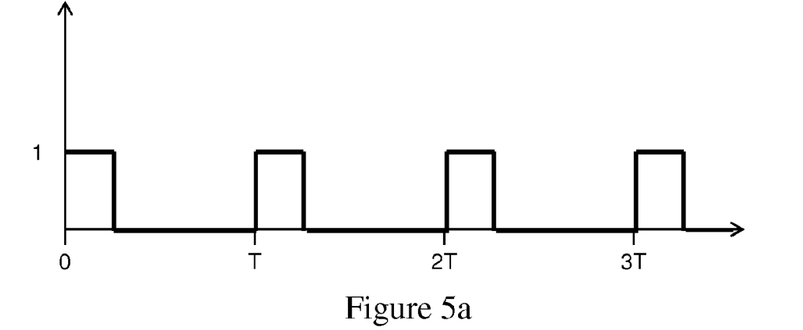
FIGS. 5a and 5b show the waveforms of the first periodic function and second periodic function according to one embodiment of the present invention respectively.
Figure 5B:
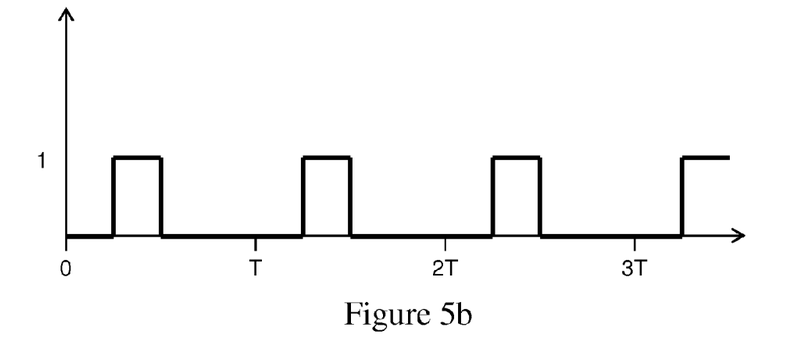
Figure 5C:
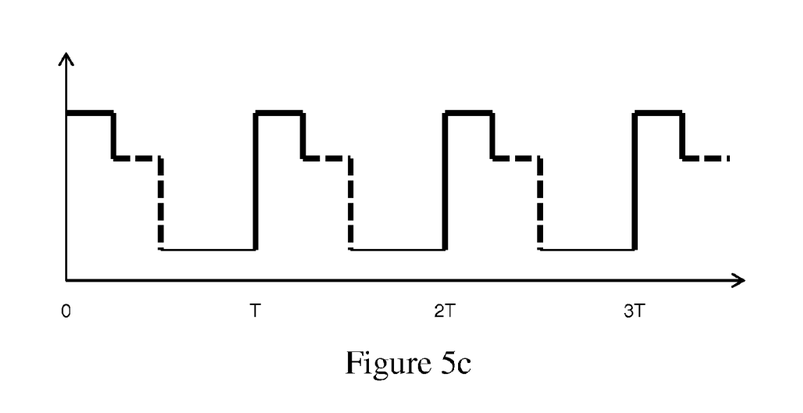
FIG. 5c shows the waveform of the modulated Raman signal in the time domain according to one embodiment of the present invention.

FIGS. 5a and 5b show a waveform in time domain of the first and second periodic functions respectively. FIG. 5c shows the waveform in time domain as the modulated Raman signal captured at the detector 24.

The first periodic function as illustrated in FIG. 5a is a square wave having unit amplitude in the first quadrant. FIG. 5b show the second periodic function in a form of square wave having unit amplitude in the second quadrant. Although FIGS. 5a and 5b show that the first and second periodic functions are square waves, the periodic functions can be in other wave forms. The shape of the wave forms are affected by the predetermined the speed of the filter wheel 34, flipping mirror 56, chopping wheel 58 or electronic optical shutter 60; and the shape of the optical filers 48 and 50. In the post-filter mode, the Raman signal is modulated by a first periodic function to obtain the first component and the Raman signal is further modulated by a second periodic function to obtain the second component. The first periodic function and the second periodic function have the same period and are orthogonal to each other. In the pre-filter mode, the excitation light having at least two wavelengths is modulated by a first periodic function to obtain the first sub-excitation light and the excitation light is further modulated by a second periodic function to obtain the second sub-excitation light. The first periodic function and the second periodic function have the same period and are orthogonal to each other. The modulated Raman signal is generated after the modulated excitation light radiated on the sample. The waveform in time domain as the modulated Raman signal captured at the detector 24 is shown in FIG. 5c. The solid line in FIG. 5c illustrates the first component and the dashed line illustrates the second component. The first component is in the first quadrant and the second component is in the second quadrant. In time domain, as shown in FIG. 5, the signal captured at the photodiode is $$S(t) = \begin{cases} A(\text{sample}), & t = (0, T/4) \\ A(\text{standard}), & t = (T/4, T/2) \\ A(\text{dark}), & t = (T/2, t) \end{cases}$$

where A(sample), A(standard), and A(dark) are the outputs from the detector 24 corresponding to the amplitudes of the sample signal, the standard signal, and the dark background, respectively, t is time and T=1/f is the time period of one cycle. In frequency domain, the above expression can be rewritten into:

$$S(t) = A(\text{dark}) + [A(\text{sample}) - A(\text{dark})] \times \left[\frac{\sqrt{2}}{\pi}\cos\left(\omega t - \frac{\pi}{4}\right)\right] +$$

$$[A(\text{standard}) - A(\text{dark})] \times \left[\frac{\sqrt{2}}{\pi}\sin\left(\omega t - \frac{\pi}{4}\right)\right] + \ldots \text{(higher order terms)};$$

where $\omega=2\pi f$. With such a modulation, the sample signal and the standard signal can be easily demodulated and separated using Fourier transform. That is, the captured photo current can be decoded to reproduce the sample signal and the standard signal through the Fourier transform output of x and y components at (the first order of) the frequency of f. By investigating the ratio of [A(sample)−A(dark)]/[A(standard)−A(dark)], the variations of the experimental conditions can be compensated, and the quantitative analysis with internal standard method is achieved.

Now turning to a method of measuring analyte within a sample according to the present invention.

Figure 6A:
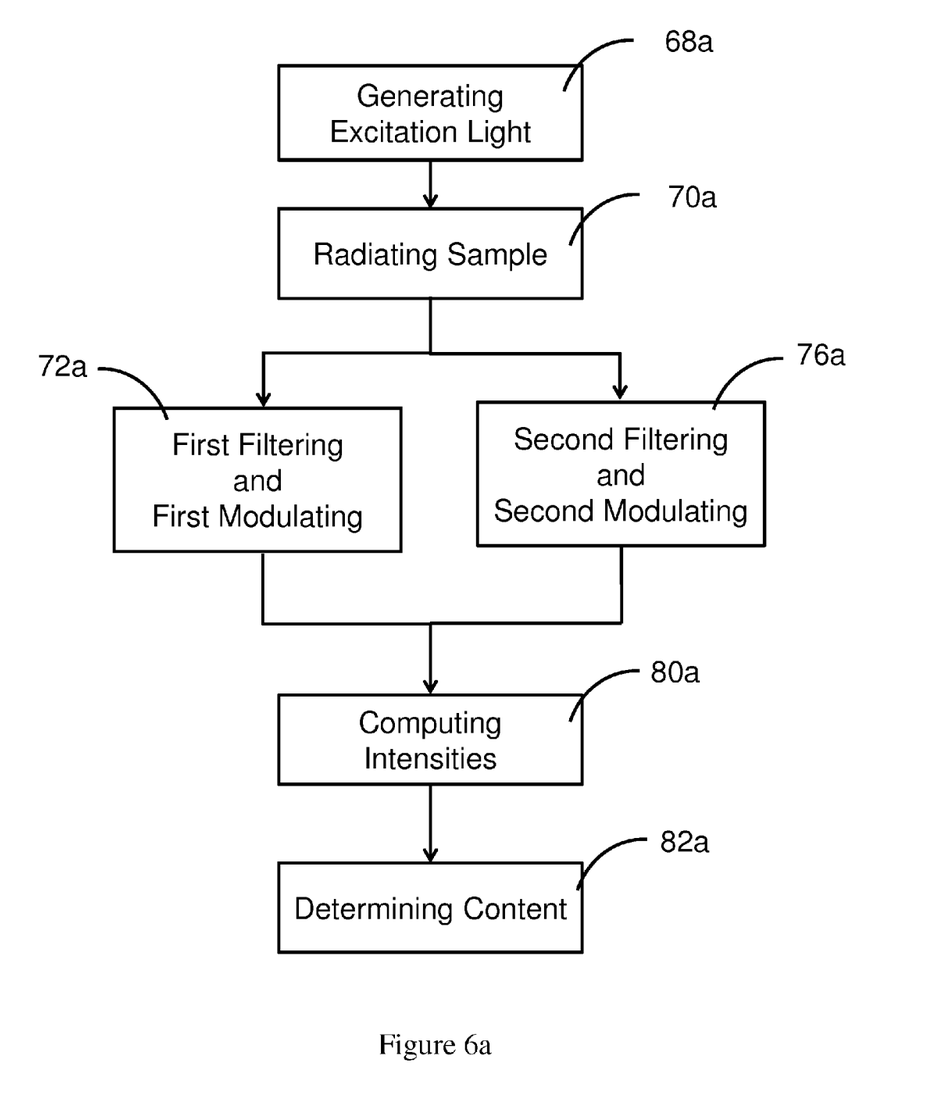
FIGS. 6a and 6b show flowcharts of the method of determining content of an analyte according to different embodiments of the present invention.
Figure 6B:
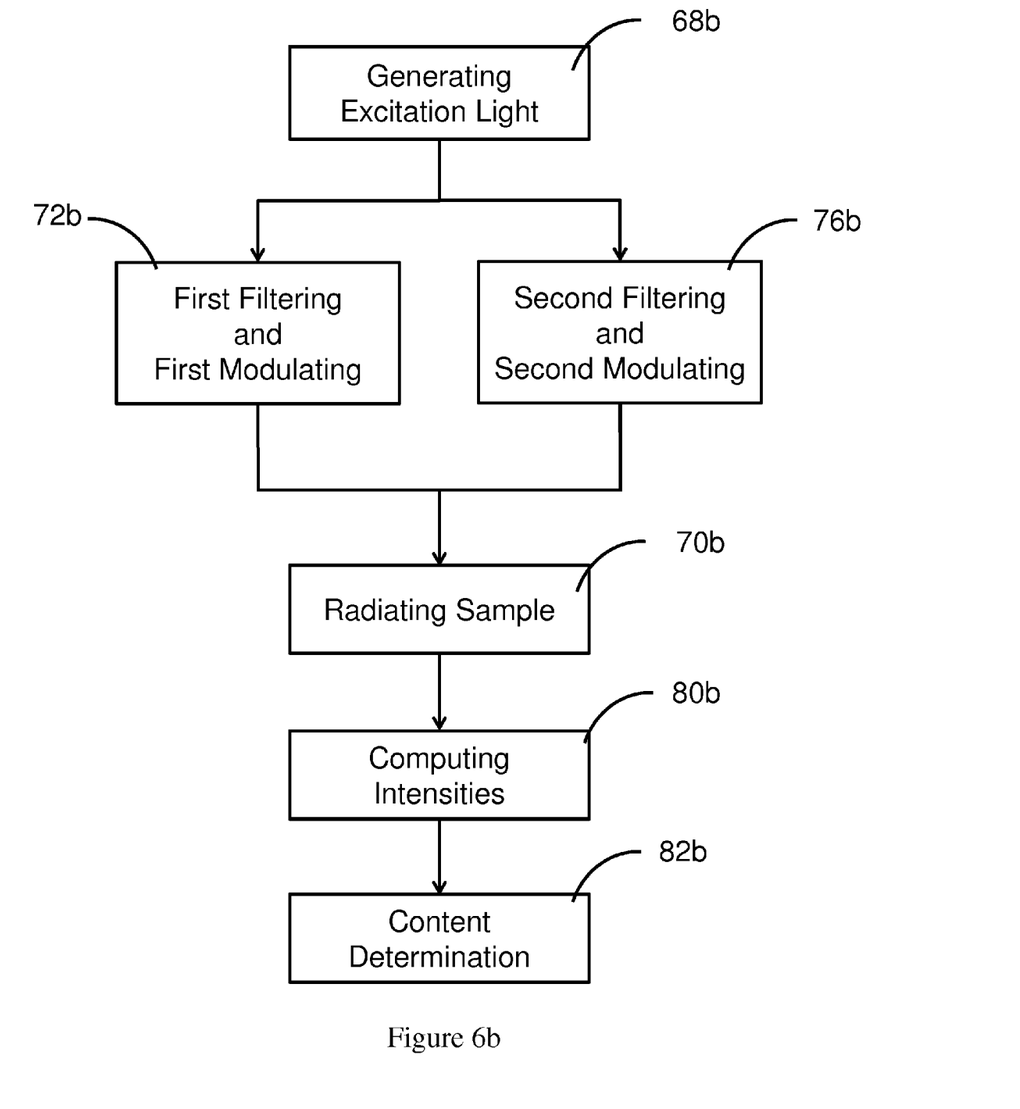

FIG. 6a and FIG. 6b illustrate two implementations of the method of measuring analyte within a sample according to the present invention.

FIG. 6a shows an implementation of a post-filtering method of the present invention. In step 68a at least one excitation light is generated and directed to the sample. An optical signal, particularly, a Raman signal is generated after the excitation light radiated the sample (step 70a). In steps 72a and 76a, the Raman signal is directed to a first optical filter 48 at a first predetermined period of time, the Raman signal is further directed to a second optical filter 50 at a second predetermined period of time and the Raman signal is blocked from reaching the detector 24 at a third predetermined period of time. The first, second and third predetermined period of time are collectively within one single completed period and the complete period is repeated for at least one time. The first predetermined period of time is the first quadrant of the completed period, the second predetermined period of time is the second quadrant of the completed period and the third predetermined period of time is the remaining amount of period of the completed period. A first component (i.e. sample signal) is obtained while allowing the Raman signal through a first optical filter 48 at a first quadrant and a second component (i.e. standard signal) is obtained while allowing the Raman signal through a second optical filter 50 at a second quadrant. The pass region of the first optical filter 48 is selected on the basis that the standard's contribution to the Raman signal of the sample is substantially stable at the pass region of the first optical filter 48 but, at the same time, the pass region should fall within a peak spectral region of the Raman signal of the sample. On the other hand, the pass region of the second optical filter 50 is selected such that the contribution of the analyte to the Raman signal of the sample is negligible at that particular wavelength. In view of the aforesaid, a standard is a substance, which should only be selected if its Raman spectrum is substantially stable within at least one of the peak spectral region of the Raman signal of the sample. The Raman signal thereby is modulated by a first periodic function to obtain the first component and is modulated by a second periodic function to obtain the second component. The first periodic function and the second periodic function have the same period and are orthogonal to each other. In step 80a, the intensities of the first component and the second component based on the first harmonic of the modulated Raman signal. Particularly, the optical module 42 is rotating at a fixed frequency f. The duration for each measurement is a predetermined period of time. The output from the detector 24 is collected by a microprocessor 26 through an A/D converter at the predetermined sampling rate. The data is processed in parallel with the data collection. The software-based demodulation is operated by calculating the first harmonic components of the sample signal and the standard signal, with

[A(sample signal)−A(dark)]

$$[A(\text{sample signal}) - A(\text{dark})] \propto \int_0^T S(t)\cos(\omega t)dt, \text{ and}$$

S(t)cos(ωt)dt, and
[A(standard signal)−A(dark)]

$$[A(\text{standard signal}) - A(\text{dark})] \propto \int_0^T S(t)\sin(\omega t)dt.$$

S(t)sin(ωt)dt.

The initial phase offset is determined by blocking either one of the band pass filters on the filter wheel 34. The above calculation is equivalent to the Fourier transform output of x and y components at (the first order of) the frequency of f. Since only one frequency is involved, the calculation is simple which does not require much computation power.

The modulated Raman signal is then demodulated by the method as discussed above and the intensity of the first component and the second component is extracted. In step 82a, the content of the analyte within the sample is determined by a ratio of said intensities of said first component and said second component. In one specific embodiment, the ratios of the intensities of the first component and the second component for the analyte and the standard only are then computed. The ratio can be represented as R=[A(sample)−A(dark)]/[A(standard)−A(dark)]. A value is obtained by having the ratio of the analyte solution minus the ratio of the standard. In other words, the value obtained can be then used to find the content of the analyte through the graph on x-axis as shown in FIG. 7b.

The Raman signal can be modulated by, but not limited to, using the optical modules 42 as described above. Any other optical modules can be used as long as the above mentioned method can be achieved.

FIG. 6b shows an implementation of a pre-filtering method of the present invention. In the first steps 68b, an excitation light with at least two wavelengths is generated and directed to the sample. In steps 72b and 76b, the excitation light is directed to a first optical filter 48 at a first predetermined period of time, the excitation light is further directed to a second optical filter 50 at a second predetermined period of time and the excitation light is blocked from reaching the sample at a third predetermined period of time. The first, second and third predetermined period of time are collectively within one single completed period and the complete period is repeated for at least one time. The first predetermined period of time is the first quadrant of the completed period, the second predetermined period of time is the second quadrant of the completed period and the third predetermined period of time is the remaining amount of period of the completed period. A first sub-excitation light with a first wavelength is obtained by allowing the excitation light passing through the first optical filter 48 and second sub-excitation light with a second wavelength is obtained by allowing the excitation light passing through the second optical filter 50. Thereby a modulated excitation light is generated. In other words, the excitation light is modulated by a first periodic function to obtain the first sub-excitation light and modulates the excitation light by a second periodic function to obtain the second sub-excitation light. The first periodic function and the second periodic function have the same period and are orthogonal to each other. In step 70b, a modulated Raman signal is generated once the modulated excitation light reaches the sample. A first component of a modulated Raman signal is generated when the first sub-excitation light interacts with the sample and a second component of a modulated Raman signal is generated when the second sub-excitation light interacts with the sample. In step 80b, the intensities of the first component and the second component based on the first harmonic of the modulated Raman signal. In one specific embodiment, the optical module 42 is rotating at a fixed frequency f. The duration for each measurement is a predetermined period of time. The output from the detector 24 is collected by a microprocessor 26 through an A/D converter at the predetermined sampling rate. The data is processed in parallel with the data collection. The software-based demodulation is operated by calculating the first harmonic components of the sample signal and the standard signal, with

[A(sample signal)−A(dark)]

$$[A(\text{sample signal}) - A(\text{dark})] \propto \int_0^T S(t)\cos(\omega t)dt, \text{ and}$$

S(t)cos(ωt)dt, and
[A(standard signal)−A(dark)]

$$[A(\text{standard signal}) - A(\text{dark})] \propto \int_0^T S(t)\sin(\omega t)dt.$$

S(t)sin(ωt)dt.

The initial phase offset is determined by blocking either one of the band pass filters on the filter wheel 34. The above calculation is equivalent to the Fourier transform output of and y components at (the first order of) the frequency of f. Since only one frequency is involved, the calculation is simple which does not require much computation power.

The modulated Raman signal is then demodulated by the method as discussed above and the intensity of the first component and the second component is extracted. In step 82b, the content of the analyte within the sample is determined by a ratio of said intensities of said first component and said second component. In one specific embodiment, the ratios of the intensities of the first component and the second component for the analyte and the standard only are then computed. The ratio can be represented as R=[A(sample)−A(dark)]/[A(standard)−A(dark)]. A value is obtained by having the ratio of the analyte solution minus the ratio of the standard. In other words, the value obtained can be then used to find the content of the analyte through the graph on x-axis as shown in FIG. 7b.

The excitation light can be modulated by, but not limited to, using the optical modules 42 as described above. Any other optical modules can be used as long as the above mentioned method can be achieved.

The computer storage medium 44 is coupled to the microprocessor 26 and the computer readable storage medium 44 is encoded with computer-readable instructions for causing the microprocessor 26 to execute or operate the steps as mentioned in the systems, optical modules 42 and the methods above.

Figure 7A:
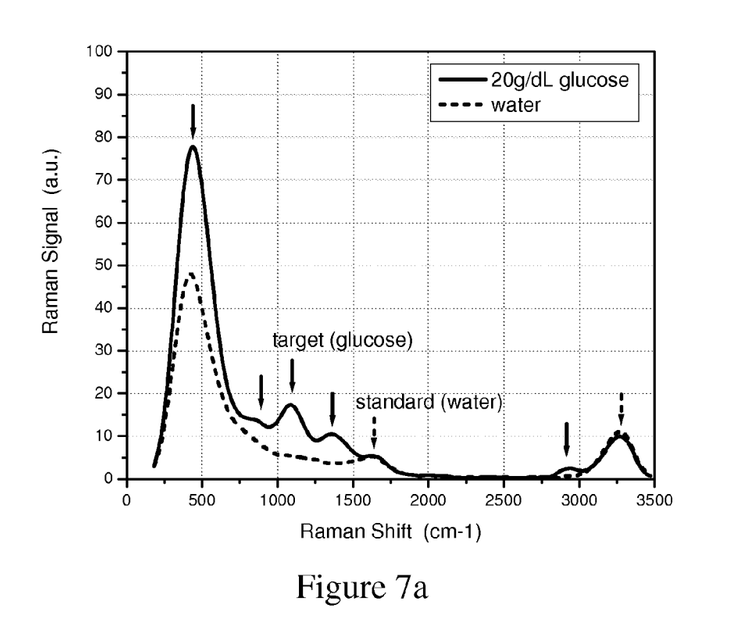
FIG. 7a shows the Raman spectra of 20 g/dL glucose solution and water obtain with a conventional Raman spectrometer with spectrograph.
Figure 7B:
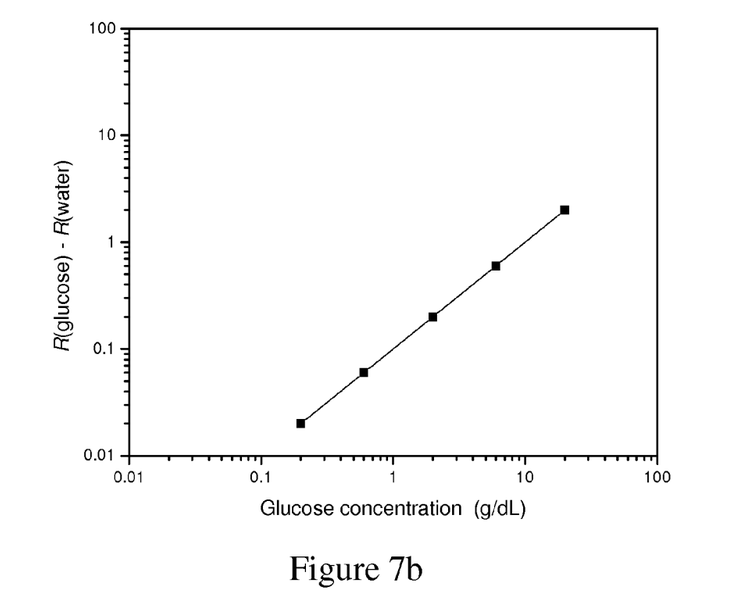
FIG. 7b shows the difference of
} the ratio obtained from glucose solution and the ratio obtained from water as plotted as a function of glucose concentration.

FIGS. 7a and 7b shows an example of the present invention. It is an example of determine the content of glucose in a solution.

FIG. 7a shows the Raman spectra of 20 g/dL glucose solution and water obtain with a conventional Raman spectrometer with spectrograph. The dashed line in FIG. 7a illustrates a spectrum of a Raman signal of a standard. In this example, the standard is water. The solid line in the same figure is a spectrum of a Raman signal of a sample. In this example, the sample is a glucose solution. The intensity of the modulated Raman signal with a Raman shift of 1100 cm-1 (i.e. first component) and the intensity of the modulated Raman signal with a Raman shift of 1640 cm-1 (i.e. second component) is opted as the sample signal and the standard signal respectively. The modulated Raman signal is generated by the methods and the systems as described above. The pair of spectral peaks of Raman shift as shown here is only an example. Other spectral peaks of Raman shift can also be chosen for the first component and the second component. The glucose peaks either at ~500 cm-1, ~900 cm-1, ~1350 cm-1, 2900 cm-1 can also be used at the sample signal; the water peak at ~3300 cm-1 can also be used at the standard signal. Moreover, other stable substances can be used at the standard signals as well other than water.

For the measurement carried out at the transmission Raman setup without spectrograph as shown in FIG. 1a, the excitation laser used is a 1064 nm diode pump solid state continuous wave laser operated 300 mW. The lenses are 1-inch BK7 lenses. The laser line filters are centered at 1064 nm with FWHM of 10 nm. The notch filters 36 are substituted with two long pass edge filters with the cutoff at 1100 nm. The detector is a 3 mm InGaAs detector. The filter wheel 34 is constructed with a blade as shown in FIG. 2 and driven by a motor, in which the band pass filter for sample is centered at 1210 nm and the one for standard is centered at 1290 nm, both with FWHM of 20 nm. The filter wheel 34 is rotating at a fixed frequency of 11.5 Hz. The duration for each measurement is 250 sec. The output from the detector is collected by a laptop computer through an A/D converter at the sampling rate of 200 kHz. The data is processed in parallel with the data collection. The software-based demodulation is operated by calculating the first harmonic components of the sample signal and the standard signal, with

[A(1100 cm-1)−A(dark)]

$$[A(1100 \text{ cm}-1) - A(\text{dark})] \propto \int_0^T S(t)\cos(\omega t)dt, \text{ and}$$

S(t)cos(ωt)dt, and
[A(1640 cm-1)−A(dark)]

$$[A(1640 \text{ cm}-1) - A(\text{dark})] \propto \int_0^T S(t)\sin(\omega t)dt.$$

S(t)sin(ωt)dt.

The initial phase offset is determined by blocking either one of the band pass filters on the filter wheel 34. The above calculation is equivalent to the Fourier transform output of x and y components at (the first order of) the frequency of 11.5 Hz. Since only one frequency is involved, the calculation is simple which does not require much computation power.

The modulated Raman signal is then demodulated by the method as discussed above and the intensity of the first component and the second component is extracted. The ratios of the intensities of the first component and the second component for the glucose solution and the water only are then computed. The ratio can be represented as $R=[A(1100\ cm^{-1})-A(dark)]/[A(1640\ cm^{-1})-A(dark)]$. A value is obtained by having the ratio of the glucose solution minus the ratio of the water. In other words, the value obtained can be then used to find the content of the analyte through the graph on x-axis as shown in FIG. 7b.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, in the aforementioned embodiments, the first component refers to the sample signal and the second component refers to the standard signal; and the first component occupies the first quadrant of the periodic function while the second component occupies the second quadrant. This is for illustration purpose and it should be noted that this is just one approach to realize the inventive idea of the present invention. Those skilled in the art would appreciate that first component can represent the standard signal while the second component represents the sample signal. Furthermore, the first component may occupy any quadrant of the periodic function while the second component occupies another quadrant of the same periodic function different from the first. When the quadrant occupied by the second component is adjacent to the quadrant of the first component, then the technique described above can be used to recover the sample and standard signals.

Furthermore, glucose is the analyte of interest in the aforementioned embodiments. However, the apparatus of the present invention could be applied in measuring other physiological substance, for instance hemoglobin or carotene in blood.

What is claimed is:

1. A method of determining the content of an analyte in a sample comprising the steps of:
   a. generating an optical signal by emitting at least one excitation light to said sample;
   b. obtaining a modulated Raman signal comprising a first component and a second component by:
      i. passing said optical signal through a first optical filter and modulating it by a first periodic function to obtain said first component; and
      ii. passing said optical signal through a second optical filter and modulating it by a second periodic function to obtain said second component;
   wherein said first periodic function and said second periodic function have same predefined period and are orthogonal to each other;
   c. computing the intensities of said first component and said second component based on the first harmonic of said modulated Raman Signal, wherein said step of computing said intensities of said first component and said second component further comprises a step of extracting an in-phase magnitude and a quad-phase magnitude of said first harmonic of said modulated Raman signal based on said predefined period; wherein said in-phase magnitude corresponds to said intensity of said first component and said quad-phase magnitude corresponds to said intensity of said second component; and
   d. determining said content of said analyte based on a ratio of said intensities of said first component and said second component.

2. The method of claim 1, wherein said first component is in a first period quadrant of said modulated Raman signal and said second component is in a period quadrant immediately after said first period quadrant.

3. The method of claim 1 wherein the duration of said modulated Raman signal is longer than said predefined period.

4. The method of claim 1, wherein said step of computing said intensities of said first component and said second component further comprises a step of passing said modulated Raman signal to an amplifier to obtain said intensities of said first component and said second component.

5. A method of determining the content of an analyte in a sample comprising the steps of:
   a. emitting an excitation light comprising a first wavelength and a second wavelength;
   b. generating a modulated excitation light from said excitation light by:
      i. passing said excitation light through a first optical filter and modulating it by a first periodic function; and
      ii. passing said excitation light through a second optical filter and modulating it by a second periodic function;
      wherein said first optical filter and said second optical filter allows said first wavelength and second wavelength to pass through respectively; said first periodic function and said second periodic function have same predefined period and are orthogonal to each other;
   c. generating an optical signal comprising a first component and a second component by directing said modulated excitation light to said sample;
   d. computing the intensities of said first component and said second component based on the first harmonic of said optical signal, wherein said step of computing said intensities of said first component and said second component further comprises a step of extracting an in-phase magnitude and a quad-phase magnitude of said first harmonic of said optical signal based on said predefined period; wherein said in-phase magnitude corresponds to said intensity of said first component and said quad-phase magnitude corresponds to said intensity of said second component; and
   e. determining said content of said analyte based on the ratio of said intensities of said first component and said second component.

6. The method of claim 5 further comprises a step of passing said optical signal through at least one laser line filter.

7. The method of claim 1 wherein the duration of said optical signal is longer than said predefined period.

8. The method of claim 5, wherein said step of computing said intensities of said first component and said second component further comprises the steps of passing said modulated Raman signal into an amplifier to obtain said intensities of said first component and said second component.

9. A measuring instrument for detecting a content of an analyte in a sample comprising:
   a. an excitation light source for irradiating said sample, thereby generating an optical signal;
   b. an optical module configured to generate a modulated Raman signal with a predefined period from said optical signal, wherein said modulated Raman signal comprises a first component and a second component, and said first component and said second component are orthogonal to each other;
c. a detector configured to receive said modulated Raman signal and convert it to an electrical signal;
d. a microprocessor coupled to said detector;
e. a computer-readable storage medium coupled to said microprocessor, said computer-readable storage medium encoded with computer-readable instructions for causing said microprocessor to execute the following steps:
  i. demodulating said modulated Raman signal based on said predefined period in order to determine a first harmonic of said modulated Raman Signal;
  ii. extracting an in-phase magnitude and a quad-phase magnitude of said first harmonic of said modulated Raman signal; wherein said in-phase magnitude and said quad-phase magnitude corresponds to the intensity of said first component and the intensity of said second component respectively; and
  iii. computing said content of said analyte based on said intensities of said first component and said second component.

10. The measuring instrument of claim 9, wherein said content of said analyte is computed based on a ratio of said intensities of said first component and said second component.

11. The measuring instrument of claim 9 further comprising:
a. a plurality of mirrors; and
b. at least one dichroic mirror;
wherein said mirrors and dichroic mirror are arranged in a way such that said coherent light source can be directed to irradiate either the front side or back side of said sample.

12. The measuring instrument of claim 9, wherein said optical module further comprises:
a. at least one first optical bandpass filter window configured to allow a first wavelength component of said optical signal to pass through;
b. at least one second optical bandpass filter window configured to allow a second wavelength component of said optical signal to pass through;
c. a filter wheel, wherein said filter wheel is divided into at least one compartment and each of said compartment contains four contiguous parts; wherein said first and second optical bandpass filter windows are mounted on the first two adjacent contiguous parts respectively and the remaining contiguous parts are configured to disable said Raman signal to pass through; and
d. a motor coupled to said filter wheel and configured to rotate said filter wheel at said predetermined period;
wherein said first component of said modulated Raman signal is a modulation of said first wavelength component and said second component of said modulated Raman signal is a modulation of said second wavelength component.

13. The measuring instrument of claim 12, wherein said first optical bandpass filter window occupies the entire first contiguous part and said second optical bandpass filter window occupies the entire second contiguous part.

14. The measuring instrument of claim 12, wherein said first and second optical bandpass filter windows substantially symmetrically cover each predetermined portion of said first two adjacent contiguous parts respectively.

15. The measuring instrument of claim 9, wherein said optical module further comprises:
a. a first optical bandpass filter window configured to allow a first wavelength component of said optical signal to pass through;
b. a second optical bandpass filter window configured to allow a second wavelength component of said optical signal to pass through; and
c. a flipping mirror configured to direct said optical signal to said first and second optical bandpass filters in predetermined timeslots;
wherein said first component of said modulated Raman signal is a modulation of said first wavelength component and said second component of said modulated Raman signal is a modulation of said second wavelength component.

16. The measuring instrument of claim 9, wherein said optical module further comprises:
a. an optical splitter configured to generate a first beam and a second beam from said Raman signal;
b. a first optical bandpass filter window configured to allow a first wavelength component of said first beam to pass through;
c. a second optical bandpass filter window configured to allow a second wavelength component of said second beam to pass through;
d. an optical switching unit configured to allow said first beam to pass through said first optical bandpass filter window and to allow said second beam to pass through said second optical bandpass filter window periodically; and
e. an optical merging unit configured to merge said first wavelength component and said second wavelength component together to form said modulated Raman signal;
wherein said first component of said modulated Raman signal is a modulation of said first wavelength component and said second component of said modulated Raman signal is a modulation of said second wavelength component.

17. The measuring instrument of claim 16, wherein said optical switching unit further comprises a rotating disk with an opening selectively allowing said optical signal to pass through.

18. The measuring instrument of claim 16, wherein said optical switching unit further comprises two liquid crystal shutters selectively allowing said optical signal to pass through.

* * * * *